United States Patent [19]

Quann et al.

[11] Patent Number: 4,686,317
[45] Date of Patent: Aug. 11, 1987

[54] PROCESS FOR REMOVING OXYGENATED COMPOUNDS OR OTHER IMPURITIES FROM HYDROCARBON STREAMS

[75] Inventors: Richard J. Quann, Moorestown; Samuel A. Tabak, Wenonah, both of N.J.

[73] Assignee: Mobil Oil Corporation, New York, N.Y.

[21] Appl. No.: 815,342

[22] Filed: Dec. 31, 1985

[51] Int. Cl.[4] .............................................. C07C 15/00
[52] U.S. Cl. .................................. 585/860; 208/331; 208/322; 585/864
[58] Field of Search ............... 208/321, 322, 327, 331, 208/332, 333, 328, 291, 950; 585/518, 533, 860, 864

[56] References Cited

U.S. PATENT DOCUMENTS

| 2,424,158 | 7/1947 | Fuqua et al. | 208/331 |
| 2,494,371 | 1/1950 | Wadley | 208/950 X |
| 2,746,985 | 5/1956 | Holder | 208/950 X |
| 2,837,587 | 6/1958 | Hogan | 585/518 X |
| 2,918,486 | 12/1955 | Binning et al. | 208/950 X |
| 3,305,592 | 2/1967 | Acciarri et al. | 260/643 |
| 3,449,462 | 6/1969 | Alders et al. | 208/327 |
| 3,565,795 | 2/1971 | Sproule et al. | 208/332 |
| 3,663,641 | 5/1972 | Hanson | 260/681.5 |
| 3,864,244 | 2/1975 | van Tassell | 208/321 |
| 3,864,245 | 2/1975 | van Tassell | 208/321 |
| 4,111,792 | 9/1978 | Caesar et al. | 208/950 X |
| 4,218,569 | 8/1980 | Chase et al. | 585/518 X |
| 4,474,647 | 10/1984 | Asselineau et al. | 585/518 X |

Primary Examiner—Andrew H. Metz
Assistant Examiner—Glenn Caldarola
Attorney, Agent, or Firm—Alexander J. McKillop; Michael G. Gilman; Lowell G. Wise

[57] ABSTRACT

A process for removing oxygenated impurities from a hydrocarbon stream includes extracting said oxygenates by a heavy organic polar solvent, water scrubbing the extracted hydrocarbon to recover dissolved solvent and combining the solvent phase from the extractor and the water phase from the scrubber and distilling to recover the solvent.

6 Claims, 1 Drawing Figure

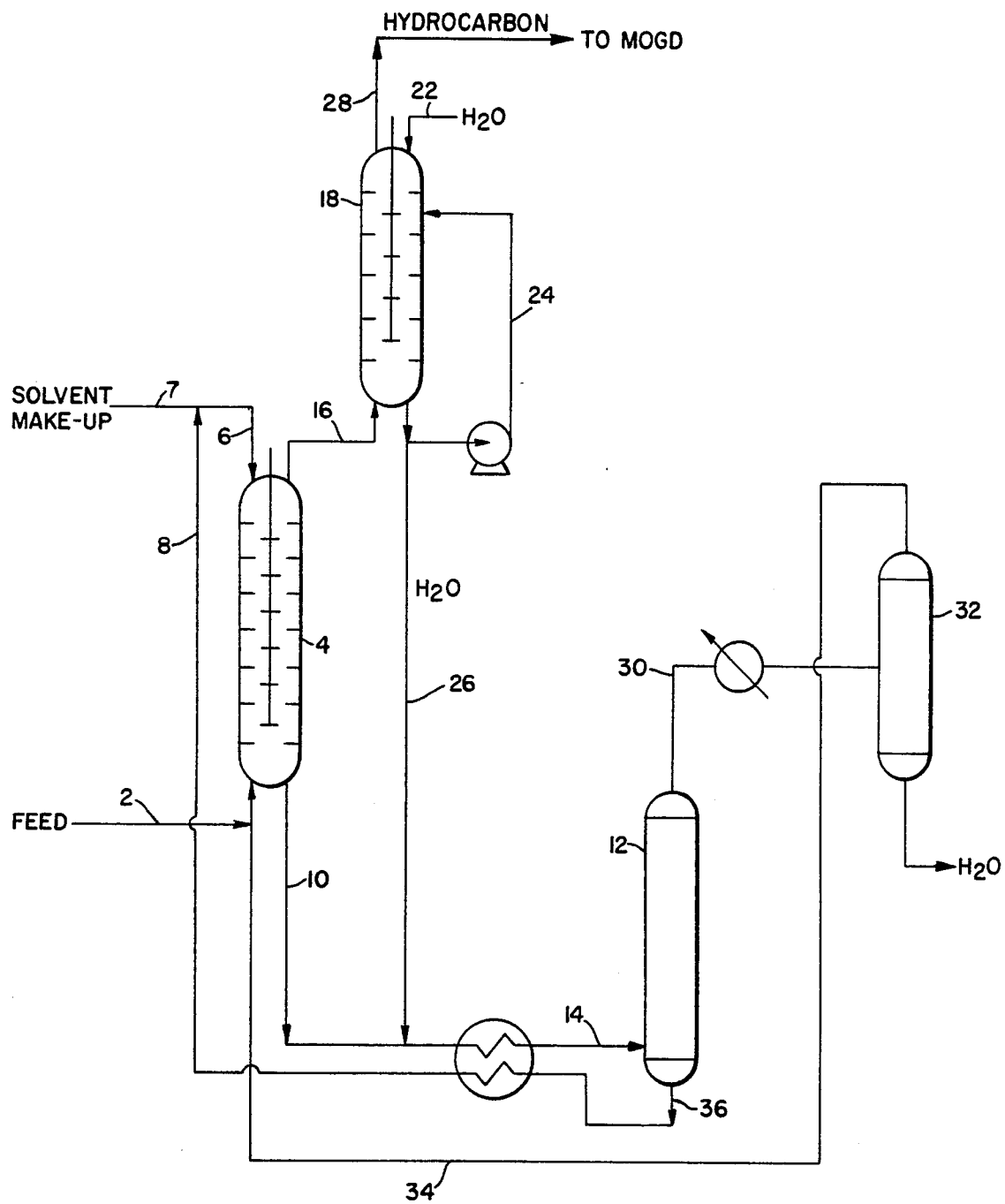

PROCESS FOR REMOVING OXYGENATED COMPOUNDS OR OTHER IMPURITIES FROM HYDROCARBON STREAMS

FIELD OF THE INVENTION

This invention relates to a process for removing non-hydrocarbon impurities from hydrocarbon streams by contacting the hydrocarbon stream with a heavy solvent in a liquid-liquid extractor. In particular, the invention is concerned with removing oxygenated impurities from Fischer-Tropsch naphtha and oligomerizing the naphtha to produce liquid hydrocarbon fuels. It is believed that the oxygenated impurities are the case of catalyst aging in the conversion of Fischer-Tropsch naphtha to higher hydrocarbons in the Mobil Olefin to Gasoline and Distillate (MOGD) process.

BACKGROUND OF THE INVENTION

Conversion of olefins to gasoline and/or distillate products in disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of ZSM-5 or releated zeolite. In U.S. Pat. Nos. 4,150,062 and 4,227,992·Garwood et al disclose the operating conditions for the Mobil Olefin to Gasoline Distillate (MOGD) process for selective conversion of $C_3+$ olefins.

The phenomena of shape-selective polymerization are discussed by Garwood in ACS Symposium Series No. 218, Intrazeolite Chemistry, "Conversion of $C_2$–$C_{10}$ to Higher Olefins over Synthetic Zeolite ZSM-5", 1983 American Chemical Society.

Typically, the process recycles cooled light hydrocarbons from a high-temperature, high-pressure separator downstream of the catalyst bed back into the reaction zone where additional olefins are converted to gasoline and distillate products. If the reaction of the olefins in converting them to distillate and gasoline is allowed to progress in the catalyst stream without any measure taken to prevent the accumulation of heat, the reaction becomes so exothermically accelerated as to result in high temperatures and the production of undesired products.

In the process for catalytic conversion of olefins to heavier hydrocarbons by catalytic oligomerization using an acid crystaline zeolite, such as ZSM-5 or related shape-selective catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the distillate mode conditions do not convert a major fraction of ethylene due to low severity conditions. While propene, butene-1 and others may be converted to the extent of 50 to 95% in the distillate mode, only about 10 to 50% of the ethylene component will be consumed.

In the high severity or gasoline mode, ethylene and the other lower olefins are catalytically oligomerized at higher teperature and moderate pressure. Under these conditions ethylene conversion rate is greatly increased and lower olefin oligomerization is nearly complete to produce an olefinic gasoline comprising hexene, heptene, octene and other $C_6+$ hydrocarbons in good yield. To avoid excessive temperatures in the exothermic reactors, the lower olefinic feed may be diluted. In the distillate mode operation, olefinic gasoline may be recycled and further oligomerized, as disclosed in U.S. Pat. Nos. 4,211,640 (Garwood and Lee) and 4,433,185 (Tabak). The above cited publications are incorporated herein by reference.

One important source of olefinic feedstocks of interest for conversion to heavier fuel products is the intermediate olefin-rich light oil or naphtha obtained from Fischer-Tropsch conversion of synthesis gas. However, these symbol materials contain, in addition to olefins, a minor amount of co-produced oxygenated hydrocarbons. It has been found that these oxygenates can interfere with catalytic oligomerization of olefins, particularly under the low severity conditions employed for making distillate and heavier hydrocarbons. It is an object of this invention to overcome catalytic deactivation by oxygenates during oligomerization by the MOGD process by extracting these non-hydrocarbon impurities from the olefinic stream prior to oligomerization.

Commonly assigned U.S. Pat. No. 4,513,156 and U.S. Ser. No. 716,317 filed Mar. 27, 1985 disclose improvements in oligomerizing olefinic Fischer-Tropsch liquids. The improvement comprises extracting oxygenates from the feedstock with a polar solvent such as water; converting the extracted feedstock in a primary stage oligomerization reactor; recovering the oxygenates and reacting them with the light hydrocarbons from the primary stage for conversion in a second stage reactor for converting the oxygenates and light hydrocarbons to heavier hydrocarbons.

U.S. Pat. No. 2,918,486 discloses the extraction of alcohols from olefine hydrocarbons with propylene carbonate. Among the olefin streams which can be treated include those obtained by the Fischer-Tropsch process. The patentee states that the process is selective for extracting alcohols in preference to organic carbonyl compounds such as aldehydes and ketones. The patent further discloses recovering dissolved solvent from the raffinate by washing the raffinate with water. Examples in the specification are limited to extracting $C_6+$ fractions from a Fischer-Tropsch process.

U.S. Pat. No. 3,305,592 discloses the separation of normal primary alkanols from admixtures thereof with olefins utilizing liquid-liquid extraction with a polar oxygen-containing solvent such as furfural, benzol alcohol, dimethylformamide and furfural alcohol.

U.S. Pat. No. 3,489,462 discloses selective solvent extraction of hydrocarbon streams using a solvent mixture comprising furfural and one or more ketones.

U.S. Pat. No. 3,565,795 discloses a process for extracting aromatic compounds from a petroleum distillate fraction by contacting the distillate fraction with hydroxyl substituted aliphatic ketones.

U.S. Pat. No. 3,663,641 discloses removing oxygenated materials from unsaturated compounds such as butadiene by a liquid-liquid phase water wash at a temperature below about 32° F. Freezing point depressants, such as alcohol, glycol, etc. can be added to avoid ice formation.

SUMMARY OF THE INVENTION

In accordance with the present invention, oxygenated impurities such as alcohols, aldehydes, ketones, and acids are extracted with hydrocarbon streams by contacting the hydrocarbon stream with a polar organic solvent containing a 2-aminoalkanol in a liquid-liquid extraction operation. The process is particularly useful in removing non-hydrocarbon impurities from olefinic naphtha obtained from the conversion of syngas by a Fischer-Tropsch process. The purified naphtha is an excellent feedstock for MOGD processing. The solvents used for extracting the oxygenates are heavy boiling relative to the oxygenated compounds contained in and removed from the hydrocarbon stream and thus separation and recovery of solvent from the oxygenated impurity can be readily accomplished by distillation. Improvements in distilling the solvent extract for solvent recovery is obtained by water washing the purified hydrocarbon stream to recover dissolved solvent and the distilling the mixture of solvent extract with the water extract.

BRIEF DESCRIPTION OF THE DRAWING

The FIGURE is a schematic diagram of the liquid extraction and solvent recovery process of the present invention.

DETAILED DESCRIPTION OF THE INVENTION

An advantageous application of MOGD is to convert Fischer-Tropsch product containing typically about 50 to about 95 wt. % $C_2$–$C_9$ light olefins to gasoline and distillate range products. The light olefinic stream produced by Fischer-Tropsch conversion is nearly an ideal feedstock for MOGD. Unfortunately the olefinic stream contains a significant amount, e.g., 0.5 to 3.0 wt. %, of oxygenated compounds, primarily ketones and aldehydes, even after extensive water washing. These oxygenates are believed to cause rapid aging of the oligomerization catalyst when processing these feedstocks under MOGD.

In accordance with this invention, the oxygenated compounds including the alcohols, ketones, aldehydes, and acids are separated from hydrocarbon streams by liquid-liquid extraction utilizing a heavy polar organic solvent. By heavy polar solvent, it is meant that the organic solvent should be immiscible with the hydrocarbons and have a boiling point higher than that of the oxygenates and the hydrocarbons. In the preferred embodiment of this invention wherein the olefinic naphtha from a Fischer-Tropsch conversion process is purified, the solvent should have a higher boiling point relative to that of the oxygenates contained therein as well as the olefins in the $C_2$–$C_9$ range. For ease of recovering extracted oxygenates from the solvent by distillation, it is preferred that the higher boiling solvent have a boiling range at least about 30° C. above the extracted compounds. Preferred solvents are oxygen-containing organic solvents which are immiscible with the hydrocarbons but not the oxygenates contained therein and are relatively high boiling relative to the oxygenates and hydrocarbons to be purified.

Polarity of the solvent may be expressed by reference to its dielectric constant and dipole moment. Preferred organic solvents have a dielectric constant greater than 20, say about 30 to 50; and a dipole moment greater than about 0.6 Debye units.

Organic solvents having these properties include compounds having carbonyl, hydroxyl, amino, ether, nitro, halogen groups, etc., such as propylene carbonate, monoethanolamine, furfural, dimethylsulfoxide and alkylene glycols. Most preferred solvents include propylene carbonate, monomethanol amine, furfural or any combination of these solvents.

While the present invention is particularly useful in removing oxygen-containing non-hydrocarbons present in a mixture of predominantly olefinic hydrocarbons such as the naphtha from Fischer-Tropsch conversion of syngas, the invention is also useful in the removal of such oxygenated compounds as alcohols, aldehydes, ketones, and acids from any type of hydrocarbon stream including aromatic, cycloaliphatic, or aliphatic hydrocarbon, e.g., paraffin, olefin, or hydrocarbon streams comprising mixtures of the various hydrocarbons. The mixtures undergoing extraction may comprise a wide boiling range mixture of hydrocarbons and oxygenates or a narrow boiling range mixture. The present invention is particularly useful for separating mixtures which cannot ordinarily be separated by distillation due to the overlap of boiling points of the hydrocarbon and oxygenates or because water extraction is not sufficient to separate the oxygenates.

It is preferred however, to purify olefinic feedstocks which can be converted to gasoline and distillate range fuels by MOGD processing. Thus, the present invention is intended primarily for purifying feedstocks rich in volatile $C_2$–$C_9$ liquid mono-olefins although more volatile and heavier hydrocarbons in the $C_2$–$C_{12}$ range may be present. The process is particularly useful in purifying $C_4$–$C_9$ olefins contained in Fischer-Tropsch naphtha.

The liquid extraction process of the present invention can best be understood by referring to the FIGURE.

A hydrocarbon feedstock such as one consisting essentially of Fischer-Tropsch naphtha fraction is introduced via feed conduit 2 to the bottom inlet of a continuous liquid-liquid extraction unit 4 wherein the feedstock is contacted in counterflow operation with the organic polar solvent of the present invention. The solvent is introduced via top solvent conduit 6 which is a combined stream composed of makeup solvent stream 7 and a recycle stream 8. The extraction unit 4 depicted is a stirred multi-stage vertical extraction column adapted for continuous operation at superatmospheric pressure (e.g., about 600–1500 kPa). It is understood that any suitable extraction equipment may be employed, including co-current, cross-current or separate stage contactors, wherein the liquid feedstock is intimately contacted with an immiscible solvent. This unit operation is described in *Kirk-Othmer Encyclopedia of Chemical Technology* (3rd. edition), 1980, pages 672–721. The oxygenate extraction step can be carried out in any counter-current multi-stage design such as a simple packed column, rotating disc column, agitated column with baffles, or mesh, or a series of single stage mixers and settlers.

The ratio of solvent to the charge mixture of hydrocarbon feedstock undergoing separation, must be sufficient to exceed the solubility of the solvent in the feedstock in order to form to distinct liquid phases, e.g., a raffinate phase of hydrocarbons containing little if any solvent, and an extract phase of solvent containing the oxygenates as the solute. Generally, between about 0.2 to 10 volumes of solvent may be used per volume of the charge mixture which is to be separated. Preferably, 0.5 to 5 volumes of solvent and, more preferably, 0.5 to 1 volume of solvent may be used per volume of feedstock which is to be purified of oxygenates.

The heavier solvent extract phase, rich in oxygenate solute, is recovered from extractor 4 via line 10 and is directed to distillation in solvent splitter 12 via line 14.

The extracted naphtha leaves the top of extractor 4 via line 16 and is directed to a water scrubber 18 for removal of solvent which has been carried from the liquid extractor by the naphtha. The FIGURE depicts a counter-current flow whereby the extracted naphtha enters the water scrubber 18 via line 16 whereas the wash water enters scrubber 18 at the top thereof via line 22. As described for liquid extractor 4, any suitable extraction equipment may be employed for water scrubber 18 including co-current, cross-current or separate stage contactors, wherein the naphtha raffinate is intimately contacted with the water for removal of the solvent from the naphtha. The water extractant containing solvent may be recycled to water scrubber 18 via line 24. The remaining solvent-containing water effluent from scrubber 18 is combined with the solvent extract phase from liquid extractor 4 via line 26 and the combined solvent-containing water via line 26 and the solvent phase containing the oxygenate solute via line 10 are mixed prior to entering solvent splitter 12 via line 14. The purified naphtha free from oxygenates and dissolved solvent leaves the water scrubber 18 via line 28 and is now ready for further processing as will be more further described below.

A novel feature of the present invention is that the solvent regeneration by distillation of the oxygenates is accomplished in the presence of water. The water provides a carrier for the oxygenates, and therefore, reduces the oxygenate content of the recycle naphtha which leaves solvent splitter 12 with the oxygenate stream 30. The naphtha is separated from the oxygenate and water phase in phase separator 32. The naphtha is recycled to liquid extractor 4 via line 34. The solvent which is recovered leaves solvent splitter 12 via line 36 and is directed to solvent recycle stream 8. Another important feature of incorporating the water wash stream from water scrubber 18 into the solvent splitter 12 is that the water aids in driving the distillation column at a temperature substantially lower than the boiling point of the heavy solvent. This results in considerable savings and utility costs.

The oligomerization catalyst preferred for use in MOGD include the medium pore (i.e., about 5–7 angstroms) shape selective crystalline aluminosilicate zeolites having a silica to alumina ratio of at least 12, a constraint index of about 1–12 and acid cracking activity of about 50–200. Representative of the shape selective zeolites are ZSM-5, ZSM-11, ZSM-12, ZSM-22, ZSM-23, ZSM-35, ZSM-38, and ZSM-48. ZSM-5 is disclosed in U.S. Pat. No. 3,702,886 and U.S. Pat. No. Re. 29,948. Other suitable zeolites are disclosed in U.S. Pat. Nos. 3,709,979 (ZSM-11); 3,832,449 (ZSM-12); 4,076,979; 4,076,842 (ZSM-23); 4,016,245 (ZSM-35); 4,046,339 (ZSM-38); and 4,375,573 (ZSM-48). The disclosures of these patents are incorporated herein by reference.

A further useful catalyst is a medium pore shape selective crystalline aluminosilicate zeolite as described above containing at least one Group VIII metal, for example Ni-ZSM-5. This catalyst has been shown to convert ethylene at moderate temperatures and is disclosed in a copending U.S. patent application Ser. No. 775,906, filed Sept. 13, 1985.

Similarly, U.S. Pat. Nos. 4,542,251 and 4,517,396 disclose oligomerizing olefins over siliceous crystalline molecular sieve catalysts which contain nickel.

The catalyst for oligomerization of the olefinic feed can be composited with a suitable binder such as alumina and shaped in the form of cylindrical extrudates of about 1–5 millimeters diameter for use in fixed bed operation or particle size for use in fluid bed operation. Other pentasil catalysts which may be employed for converting lower olefins include a variety of medium pore (~5 to 9 A) siliceous materials such as borosilicates ferrosilicates, and/or aluminosilicates disclosed in U.S. Pat. Nos. 4,414,423; 4,417,086; and 4,517,396, incorporated herein by reference.

The general operating parameters for MOGD in the process of the present invention can be defined by stating that the process is carried out at pressures from about 0–2000 psig, at temperatures ranging from about 350°–700° F., and at a space velocities of 0.2–10 LHSV. It is to be immediately understood that the above recitation of ranges of pressure, space velocity, and temperature is not intended to mean that all operations within the above set forth limits will result in producing the desired results of the invention. On the contrary, what is meant by the above limits concerning temperature, pressure, and space velocity is best expressed in a negative way. In other words operations outside the ranges specifically set forth will not result in the improved process of this invention. It is well known in the art that there is a correlation between temperature, pressure, and space velocity with respect to the severity of a given chemical reaction. Quite simply put, the instant invention is concerned with the conversion of an olefinic stream to gasoline and distillate fuels.

To operate the MOGD to obtain a greater proportion of distillate fuels, the reaction is run at moderate temperature of 375°–600° F. and relatively high pressure of about 600–1200 psig. On the other hand, for producing a greater proportion of gasoline, the operation is run at elevated temperature 450°–700° F. and more moderate pressure of about 50–400 psig. The MOGD reactor can be fixed, moving or fluidized bed.

EXAMPLE 1

Synthol Light Oil (SLO) naphtha was contacted with an equal volume of solvents in a magnetically stirred flask for five minutes to allow for the transfer and equilibration of oxygenates between the two phases. After this, the light naphtha and heavy solvent were allowed to phase separate. The naphtha phase was then sampled and analyzed for its oxygenate content. The volume loss of naphtha on contact with solvent was also monitored for selected solvents and solvent mixtures. Using this batch extraction procedure, the equilibrium portioning of oxygenates between solvent and naphtha phases could be determined. This provided a basis for selecting the most appropriate solvent for continuous counter-current extractor studies.

The ten heavy solvents examined by batch equilibrium studies are listed in Table 1. In addition to these heavy solvents, aqueous solutions of HCl, NaOH and methanol were also tested. Heavy solvents are preferred from a process standpoint because of their high boiling points relative to that of the oxygenates and olefins in the $C_2$–$C_6$ range. As has been discussed previously, this is advantageous for solvent regeneration when the oxygenates are separated from the spent solvent by distillation. The composition of fresh synthol naphtha and of the extracted naphtha for the various solvents are given in Table 2. Also listed in Table 2 is the percent of total oxygenates extracted from the naphtha by each solvent. Furfural, propylene carbonate and 2-aminoethanol are among the most effective solvents. Successive batch extractions were also performed for selected solvents followed by a water wash. These results are presented in Table 3. Each batch extraction step and the final water wash used equal volumes of solvent and naphtha. Again, propylene carbonate, furfural and 2-aminoethanol have the highest affinity for oxygenates in successive equilibrium batch extractions. It is also evident that successive batch extractions is effective in further reducing oxygenate content. Solvent mixtures were also tested for their affinity and selectivity for oxygenates versus olefins. These results are shown in Table 4. Generally, mixing of solvents resulted in a capacity for oxygenates that was similar to the solvent that had the lower affinity. In some cases, however, mixing of solvents proved beneficial by reducing the naphtha dissolution into the solvent phase. The extent of naphtha loss to the solvent phase for selected solvents and solvent mixtures is shown in Table 5.

TABLE 1

| Heavy Solvents Tested In Batch Equilibrium Studies | | |
|---|---|---|
| | Boiling Point (C.) | Dielectric Coefficient |
| Dimethyl Sulfoxide | 189 | 46.7 |
| Ethylene Glycol | 197.3 | 38.7 |
| Dipropylene Glycol | 231.0 | 30 (est.) |
| Diethylene Glycol | 244.8 | 29.5 |
| Triethylene Glycol | 288 | — |
| Tetraethylene Glycol | 327 | — |
| Furfural | 161.8 | 41.9 |
| 2-Aminoethanol | 172 | 37.72 |
| Diethanol Amine | 134 | 2.81 |
| Propylene Carbonate | 241.7 | 64.6 |

TABLE 2

Oxygenate Content of Fresh Synthol Naphtha* Before and After Batch Extraction with Solvents (1 vol. Naphtha/1 Vol. Solvent)

| | Fresh Naphtha | Dimethyl Sulfoxide | Ethylene Glycol | Dipropylene Glycol | 2-Aminoethanol | Furfural | Triethylene Glycol | Diethanol Amine |
|---|---|---|---|---|---|---|---|---|
| Oxygenate (Wt. %): | | | | | | | | |
| Propanol | 0.34 | 0.03 | 0.06 | 0.06 | 0.03 | 0.02 | 0.12 | — |
| Butanol | 0.22 | 0.05 | 0.07 | 0.06 | 0.02 | | | |
| Butanal | | | | | | 0 | 0.09 | 0.04 |
| 2-Butanone | 0.87 | 0.22 | 0.39 | 0.25 | 0.25 | 0.12 | 0.34 | 0.49 |
| Isobutanol | 0.01 | 0 | 0 | 0 | 0 | 0 | 0 | 0 |
| 3 Methyl-2 Butanone | 0.12 | 0.05 | 0.08 | 0.05 | 0.08 | 0.03 | 0.06 | 0.09 |
| 1-Butanol | 0.02 | 0 | 0 | 0 | 0 | 0 | 0 | 0 |
| 2-Pentanone | 0.31 | 0.12 | 0.22 | 0.13 | 0.15 | 0.07 | 0.16 | 0.22 |
| Pentanal | 0.03 | 0.01 | 0.02 | 0.01 | 0 | 0 | 0.01 | 0 |
| Total | 1.92 | 0.48 | 0.84 | 0.56 | 0.53 | 0.24 | 0.78 | 0.84 |
| Extracted % | — | 75 | 56.3 | 70.8 | 72.4 | 87.5 | 59.4 | 48.1 |

| | Propylene Carbonate | Diethylene Glycol | Tetraethylene Glycol | $H_2O$ | 0.2N HCl | 0.2N NaOH | 25% MeOH—$H_2O$ |
|---|---|---|---|---|---|---|---|
| Oxygenate (Wt. %) | | | | | | | |
| Propanal | — | — | — | 0.22 | 0.10 | — | — |
| Butanal | 0 | 0.10 | 0.09 | 0.14 | 0.13 | 0.11 | 0.07 |
| 2-Butanone | 0.16 | 0.34 | 0.26 | 0.27 | 0.39 | 0.37 | 0.30 |
| Isobutanol | 0 | 0 | 0 | 0 | 0 | 0 | 0 |
| 3 Methyl-2 Butanone | 0.06 | 0.07 | 0.06 | 0.07 | 0.09 | 0.09 | 0.07 |
| 1-Butanol | 0 | 0 | 0 | 0.01 | 0 | 0.01 | 0 |
| 2-Pentanone | 0.14 | 0.17 | 0.17 | 0.15 | 0.24 | 0.24 | 0.19 |
| Pentanal | 0 | 0.01 | 0.02 | 0.02 | 0.03 | 0.01 | 0.01 |
| Total | 0.38 | 0.69 | 0.60 | 0.88 | 0.98 | 0.86 | 0.64 |
| Extracted % | 76.0 | 56.3 | 52.0 | 54.2 | 49.0 | 45.6 | 59.5 |

*All naptha water washed prior to extraction studies

TABLE 3

Oxygenate Content of Synthol Naphtha After Successive Equilibrium Batch Extractions and $H_2O$ Washing of Extracted Naphtha

| Solvent | Triethylene Glycol | | | Diethanol Amine | | | Propylene Carbonate | | |
|---|---|---|---|---|---|---|---|---|---|
| Extraction Step | 1 | 2 | $H_2O$ Wash | 1 | 2 | $H_2O$ Wash | 1 | 2 | $H_2O$ Wash |
| Oxygenate (Wt. %): | | | | | | | | | |
| Propanol | .12 | .09 | .03 | — | — | — | — | — | — |
| Butanol | .09 | .05 | .04 | .04 | .01 | 0 | .05 | .01 | .01 |
| 2-Butanone | .34 | .15 | .08 | .49 | .33 | .16 | .15 | .04 | .02 |
| Isobutanol | 0 | 0 | 0 | 0 | 0 | 0 | 0 | 0 | 0 |
| 3 Methyl-2 Butanone | .06 | .04 | .03 | .09 | .07 | .06 | .03 | .01 | .01 |
| 1-Butanol | 0 | 0 | 0 | 0 | 0 | 0 | 0 | 0 | 0 |
| 2-Pentanone | .16 | .09 | .07 | .22 | .18 | .18 | .08 | .03 | .02 |
| Pentanal | 0.1 | 0.1 | 0 | 0 | 0 | 0 | 0.1 | 0 | 0 |
| Total | .78 | .42 | .25 | .84 | .59 | .36 | .32 | .09 | 0.6 |
| Extracted % | 59.4 | 78.1 | 87.0 | 46.8 | 62.7 | 77.2 | 79.8 | 94.3 | 96.2 |
| Solvent | 2-Aminoethanol | | | Furfural | | | Dipropylene Glycol | | |

TABLE 3-continued

Oxygenate Content of Synthol Naphtha After Successive Equilibrium Batch Extractions and H₂O Washing of Extracted Naphtha

| Extraction No. | 1 | 2 | H2O Wash | 1 | 2 | H2O Wash | 1 | 2 | 3 | H2O Wash |
|---|---|---|---|---|---|---|---|---|---|---|
| Oxygenates (wt %): | | | | | | | | | | |
| Propanal | .03 | — | — | .02 | — | — | .12 | — | — | — |
| Butanal | .02 | .01 | 0 | 0 | .01 | .01 | .10 | .05 | .03 | .01 |
| Butanone | .25 | .08 | .04 | .12 | .03 | .02 | .40 | .17 | .09 | .02 |
| Isobutanol | 0 | 0 | 0 | 0 | 0 | 0 | 0 | 0 | 0 | 0 |
| 3-Methyl-2-Butanone | .08 | .04 | .04 | .03 | .01 | .01 | .07 | 0.4 | 0.2 | .01 |
| 1-Butanol | 0 | 0 | 0 | 0 | 0 | 0 | 0 | 0 | 0 | 0 |
| 2-Pentanone | .15 | .07 | .05 | .07 | .02 | .02 | .18 | .09 | .06 | .02 |
| Pentanal | 0 | 0 | 0 | 0 | 0 | 0 | .01 | .01 | 0 | 0 |
| Total (wt %) | 0.53 | .23 | .13 | .24 | .07 | .06 | 0.88 | 0.36 | .20 | .0 |
| Extracted (%) | 72.4 | 85.4 | 91.8 | 87.5 | 95.6 | 96.2 | 54.2 | 77.2 | 84.4 | 96.2 |

TABLE 4

Oxygenate Content of Naphtha After Batch Extraction With Solvent Mixtures (50:50 Proportions)

| | Fresh Naphtha | 2AE + PC | 2AE + Furfural | Furfural + TEG | PC + TEG |
|---|---|---|---|---|---|
| Oxygenate (wt %) | | | | | |
| Propanal | 0.34 | 0.06 | 0.01 | 0.04 | 0.05 |
| Butanal | 0.22 | 0.04 | 0 | 0.04 | 0.05 |
| 2-Butanone | 0.81 | 0.24 | 0.19 | 0.25 | 0.24 |
| Isobutanal | 0.01 | 0 | 0 | 0 | 0 |
| 3-Methyl-2-Butanone | 0.12 | 0.07 | 0.08 | 0.05 | 0.05 |
| 1-Butanol | 0.02 | 0 | 0 | 0 | 0 |
| 2-Pentanone | 0.31 | 0.14 | 0.18 | 0.13 | 0.13 |
| Pentanal | 0.03 | 0 | 0 | 0.01 | 0.01 |
| Total (wt %) | 1.92 | 0.55 | 0.46 | 0.52 | 0.53 |
| Extracted (%) | — | 71.4 | 76.0 | 72.9 | 72.4 |

*2AE - 2-Aminoethanol
PC - Propylene Carbonate
TEG - Tetraethylene Glycol

TABLE 5

Naphtha Dissolution Into Solvents And 50:50 Solvent Mixtures

| Solvent | Volume % of Naphtha Dissolved |
|---|---|
| Furfural | 27 |
| 2 Aminoethanol | 1 |
| Propylene carbonate | 10 |
| Dimethyl Sulfoxide | 8 |
| Tetraethylene Glycol | 0 |
| Diethanol Amine + Water | 0 |
| 2 Aminoethanol + Propylene Carbonate | 0 |
| 2 Aminoethanol + Furfural | 1 |
| Tetraethylene Glycol + Furfural | 7 |
| Tetraethylene Glycol + Propylene Carbonate | 9 |

EXAMPLE 2

Continuous extraction studies were conducted on a multi-stage counter current extractor. The unit was purchased from York Process Equipment Co., Fairfield, N.J. and had maximum throughput capacity of 3600 cc/hour. The extraction column contained 12 well mixed or agitated stages separated by wire mesh containing zones. Mixing in the stages was accomplished by a single central shaft having a propeller-like agitator in each stage. Separation of phases occurred in the wire mesh containing zones between the well mixed stages.

Operation of the continuous extractor was straightforward. Naphtha, being the lighter phase, was charged to the bottom inlet on the column. The heavier solvent phase entered through the top inlet and exited from the bottom of the column. The preferred operation of the extractor is to have the continuous phase correspond to the phase with the highest throughput or flow rate. In this case, the continuous phase was the naphtha phase and the dispersed phase was the solvent. The phase interface was maintained below the naphtha inlet at the bottom of the column. Naphtha and solvent flow rates were controlled by Milton Roy controlled volume pumps.

Propylene carbonate was selected as the solvent for studies with the continuous counter current extractor. This selection was based on its relatively high efficiency for extracting oxygenates, its high boiling point, and its non-toxicity. Furfural and 2-aminoethanol are also satisfactory insofar as extraction efficiency is concerned, but furfural forms an azeotrope with H₂O and would, therefore, be difficult to regenerate and 2-aminoethanol is a solvent requiring more safeguards in handling and exhibits an overall lower capacity for olefins than propylene carbonate. The oxygenate content of synthol naphtha's after continuous counter-current extraction are shown in Tables 6 and 7. The analyses reported in these tables are from small samples taken on line, not from cumulative batches. Extraction efficiencies were generally quite high under the conditions studied here. A naphtha to solvent volume ratio of 4 (Run Y1) did, however, have a considerably lower extraction efficiency than the lower ratios of the other runs. Run Y9A differed from the other extraction runs in that the continuous phase was the solvent and the dispersed phase was the naphtha. In this mode of operation the interface between the phases is at the top of the extraction column. This did not seem to have an effect on extraction efficiency. The apparent increase in percent extracted with increasing flowrates (Runs Y10D, Y11D, and Y12D) was probably an artifact of the start-up procedure. During start-up, the column is first flooded with fresh naphtha before solvent is added. Hence, at the lower feed rates of Runs Y10D and Y11D, the system had probably not reached steady-state in the time allotted, resulting in an incomplete purge of the initial 480 cc charge of fresh naphtha.

Run Y12 was used to generate several gallons of extracted feedstock for testing in an MOGD pilot plant. Analysis of an on-line sample indicated that only 0.03 percent of the oxygenates remained after extraction. Analysis of the cumulative sample revealed that 0.17 percent oyxgenates remained. These results, along with analysis of the spent solvent, are reported in Table 8. The extracted naphtha was also water washed in the York extractor using a naphtha to water volume ratio of 2. As shown in Table 8, this reduced the dissolved solvent content of the naphtha to below the detection limit of the analytical test method. The oxygenate content of the water washed naphtha remained essentially the same.

The effect of extraction on the composition of hydrocarbons was tested. The data in Table 9 demonstrates that extraction of the naphtha with the solvent has only a minor effect on the composition and no significant selectivity for specific olefins or other hydrocarbons.

Table 10 contains the calculated compositions for a 15,000 BPD commercial extraction process as shown schematically in the FIGURE.

TABLE 6

Naphtha Oxygenate Content After Continuous Multistage Extraction With Propylene Carbonate

| Run No. | Fresh Naphtha | Y1 | Y2A | Y2B | Y3A | Y3B | Y8A | Y9A |
|---|---|---|---|---|---|---|---|---|
| Naphtha cc/Hr | | 3600 | 3600 | 3600 | 3600 | 3600 | 720 | 3600 |
| Naphtha/Solvent Volume Ratio | | 4 | 2 | 2 | 1 | 1 | 2 | 2 |
| Time on Stream | | 20 | 20 | 40 | 20 | 40 | 20 | 20 |
| Oxygenates (wt %) | 0.26 | 0.03 | 0.02 | 0.02 | 0.03 | 0.04 | 0.03 | 0.02 |
| Propanol | 0.20 | 0.07 | 0.01 | 0.01 | 0.01 | 0.01 | 0.01 | 0.01 |
| 2-Butanone | 0.76 | 0.13 | 0.01 | 0 | 0 | 0 | 0 | 0.01 |
| Isobutanol | 0.01 | 0.01 | 0.01 | 0.01 | 0.01 | 0.01 | 0.01 | 0.01 |
| 3-Methyl-2-Butanone | 0.10 | 0.04 | 0.01 | 0.01 | 0 | 0 | 0 | 0.01 |
| 1-Butanol | 0.02 | 0.0 | 0 | 0 | 0 | 0.01 | 0 | 0 |
| 2-Pentanone | 0.28 | 0.10 | 0.02 | 0.01 | 0 | 0 | 0 | 0.02 |
| Pentanal | 0.03 | 0.01 | 0 | 0 | 0 | 0 | 0 | 0 |
| Total (wt %) | 1.66 | 0.39 | 0.08 | 0.06 | 0.05 | 0.07 | 0.05 | 0.08 |
| Extracted (%) | — | 76.5 | 95.2 | 96.4 | 97.0 | 95.8 | 97.0 | 95.2 |

TABLE 7

Naphtha and Spent Solvent Oxygenate Content After Continuous Extraction

| | Fresh Naphtha | Y10 | Y11 | Y12 | Fresh Naphtha | Y13NW | Y13 Solvent |
|---|---|---|---|---|---|---|---|
| Naphtha Flow Rate cc/hr | | 720 | 1800 | 3600 | | 3600 | 3600 |
| Naphtha/Solvent Volume Ratio | | 2 | 2 | 2 | | 2 | 2 |
| Time on Stream (min) | | 80 | 80 | 80 | | | |
| Oxygenates (wt %) | | | | | | | |
| Propanel | 0.68 | .03 | .02 | .02 | .010 | .03 | 0.70 |
| Butanal | 0.30 | .03 | .02 | .01 | 0.85 | .02 | .42 |
| 2-Butanone | 1.42 | .02 | .01 | 0 | 0.97 | .01 | 1.41 |
| Isobutanol | 0.06 | 0 | .01 | 0 | 0.06 | 0 | .10 |
| 3-Methyl-2-Butanone | 0.09 | .01 | .01 | 0 | 0.13 | 0 | .11 |
| 1-Butanol | 0.12 | 0 | 0 | 0 | 0.08 | 0 | .20 |
| 2-Pentanoe | 0.33 | .02 | .02 | 0 | 0.19 | .01 | .29 |
| Pentanal | 0.03 | 0 | 0 | 0 | 0.10 | .01 | .03 |
| Total (wt %) | 3.03 | .11 | .09 | 0.03 | 2.48 | .08 | 3.16 |
| Extracted (%) | | 96.4 | 97.0 | 99.0 | | 96.8 | |

TABLE 8

Simulation of Commercial Extraction Operation Using Pilot Plant Extractor, Stream Compositions

| | Extracted Napthta | Water Washed Naphtha | Spent Solvent | Wash Water |
|---|---|---|---|---|
| Oxygenates (wt %) | | | | |
| Propponal | 0.04 | 0.04 | 0.72 | 0.013 |
| Butanal | 0 | 0 | 0.37 | 0 |
| 2-Butanone | 0.03 | 0.03 | 1.38 | 0 |
| Isobutanol | 0 | 0 | 0.11 | 0 |
| 3-Methyl-2-Butanone | 0.09 | 0.11 | 0.11 | 0 |
| 1-Butanol | 0 | 0 | 0.20 | 0 |
| 2-Pentanone | 0 | 0 | 0.29 | 0 |
| Pental | 0.01 | 0.01 | 0.04 | 0 |
| Total Oxygenates (wt %) | 0.17 | 0.18 | 3.22 | 0.013 |
| Naphtha (wt %) | — | — | 7.46 | 0.25 |

TABLE 8-continued

Simulation of Commercial Extraction Operation Using Pilot Plant Extractor. Stream Compositions

|  | Extracted Naphtha | Water Washed Naphtha | Spent Solvent | Wash Water |
|---|---|---|---|---|
| Propylene Carbonate | 0.59 | <100 ppm | — | |
| Run No. (Sample No.) | Y12 | Y12W | Y12 Solvent | |

TABLE 9

Effect of Extraction on Naphtha Composition (wt %)

|  | Fresh Naphtha | Extracted Naptha | In Solvent |
|---|---|---|---|
| 1-Pentene | 20.68 | 24.06 | 22.90 |
| 1-Hexene | 29.95 | 31.42 | 34.96 |
| Branched & Olefins | 14.23 | 15.29 | 14.68 |
| Non & Olefins | 5.36 | 5.67 | 6.59 |
| Saturates | 15.00 | 13.23 | 10.80 |
| Aromatics | 0.60 | 0.47 | 2.87 |
| Total Olefins | 70.23 | 76.44 | |

TABLE 10

Stream Composition in Barrels/Day
Solvent: Propylene Carbonate
Naphtha: Fischer-Tropsch Product

| Stream No. From Figure | | Naphtha | Oxygenates | Solvent | H$_2$O | Total |
|---|---|---|---|---|---|---|
| 2 | Naphtha Feed | 14,625 | 375 | — | — | 15,000 |
| 16 | Extracted Naphtha | 14,625 | 25 | 50 | — | 14,700 |
| 28 | Washed Naphtha | 14,625 | 25 | 1 | — | 14,651 |
| 26 | Spent Wash Water | — | — | 49 | 4875 | 4,924 |
| 10 | Spent Solvent | 517 | 365 | 5122 | — | 6,004 |
| 34 | Recycle Naphtha | 517 | 15 | — | — | 6,536 |
| 33 | Spent Water & Oxygenates | — | 350 | — | 4875 | 5,225 |
| 36 | Regenerated Solvent | — | — | 5171 | — | 5,171 |
| 22 | Water Feed | — | — | — | 4872 | 4,872 |
| 7 | Fresh Solvent | — | — | 1 | — | — |

EXAMPLE 3

MOGD was run on a unit which contained a single fixed bed which was operated isothermally and single pass. The operating conditions were 1 WHSV, 600 psig and 450° F. A temperature of about 450° F. was maintained throughout the course of each run. Catalyst deactivation was monitored by the change in product selectivity and the decrease in feed olefin conversion. The catalyst was H-ZSM-5. The only significant difference between each sample was in the nature of the feedstock. The feedstocks used in the four samples are shown in Table 11 and summarized below:

| Sample No. | Feedstock Description |
|---|---|
| 1 | Model compound blend of Pentene and Hexene |
| 2 | Solvent Extracted and Water-Washed Synthol Naphtha |
| 3 | Untreated Synthol Naphtha |
| 4 | Pentene/Hexene Blend Doped with H$_2$O and 100 ppm Propylene Carbonate |

The composition of the feedstocks are provided in detail in Table 11. The purpose of Sample No. 1 was to provide a low fouling base case with a feedstock that has no oxygenate impurities. The purpose of Samples 2 and 3 were to demonstrate the effectiveness of the solvent extraction approach as a means of decreasing catalyst aging. Sample 4 used a model compound feedstock coped with H$_2$O and the solvent propylene carbonate to determine if these impurities from the extraction process have significant effect on catalyst aging.

The effect of feedstock composition on catalyst aging as measured by distillate yield, selectivity, and pentene conversion can be seen in Tables 12-15 wherein material balances for these runs are given. The decline in catalyst activity due solely to the presence of oxygenates is evident in the tables where selectivity changes from distillate to gasoline with time on stream. The feedstock for Sample 1 contained the same olefins but did not contain oxygenates. Consequently, little deactivation was observed for this run compared to Sample 3.

The effect of oxygenates on catalyst activity in Sample 3 was both immediate and progressive as evidenced by comparison of the initial distillate yields shown in Tables 12 and 14.

The effects of feedstock saturation with H$_2$O (Sample 4; balances 1, 2, 3) and doping with the solvent propylene carbonate (Sample 4; balances 4, 5) are shown in the tables. A comparison of Sample 1 with Sample 4 reveals that neither of these impurities has an effect on distillate yield, selectivity or pentene conversion (Tables 12 and 15).

The effects of synthol feedstocks on catalyst aging are shown in the tables for distillate yields, gasoline yield and bromine number. The untreated naphtha (Sample 3) poisons the catalyst to the extent that distillate is not produced even in the first material balance. This probably reflects strong adsorption poisoning of catalytic sites by the oxygenates. The solvent extracted/water washed synthol naphtha will convert initially to distillate (Sample 2), after which deactivation is rapid.

TABLE 11

Composition of Charge Stocks

| Run No. Charge No. | 1 | 2 | 3 | 4 | 4 |
|---|---|---|---|---|---|
| Propene | 0 | 0 | 0 | 0 | 0 |
| Propane | 0 | 0 | 0 | 0 | 0 |
| Butenes | .236 | .648 | .341 | .236 | .236 |
| 1 Butane | .054 | 0 | .193 | .054 | .054 |
| N Butanes | 0 | .376 | 0 | 0 | 0 |

TABLE 11-continued

Composition of Charge Stocks

| Run No. Charge No. | 1 | 2 | 3 | 4 | 4 |
|---|---|---|---|---|---|
| Pentenes | 46.740 | 35.650 | 30.299 | 46.740 | 35.650 |
| Pentanes | .022 | 7.686 | 5.42 | .044 | 7.686 |
| Hexenes | 41.223 | 41.232 | 44.289 | 41.223 | 41.232 |
| $C_6+$ non-olefins + $C_7$ olefins | 11.725 | 14.408 | 19.458 | 11.703 | 14.408 |
| Oxygenates (wt %) | | | | | |
| Propanal | — | .04 | 0.68 | — | — |
| Butanal | — | — | 0.30 | — | — |
| 2-Butanone | — | .03 | 1.42 | — | — |
| Isobutanol | — | — | 0.06 | — | — |
| 3-Methyl-2-Butanone | — | .11 | 0.09 | — | — |
| 1-Butanol | — | — | 0.12 | — | — |
| 2-Pentanone | — | — | 0.33 | — | — |
| Pentanal | — | .01 | 0.03 | — | — |
| Total (wt %) | — | 0.18 | 3.03 | — | — |
| Propylene Carbonate (wt %) | — | <0.01 | — | — | .01 |
| $H_2O$ (ppm) | — | 135 | 167 | 149 | 149 |

TABLE 12

MATERIAL BALANCE DATA FOR SAMPLE 1

| BALANCE NO. | 1 | 2 | 3 | 4 | 5 | 6 | 7 |
|---|---|---|---|---|---|---|---|
| DAYS ON STREAM | 1 | 2 | 3 | 4 | 5 | 6 | 8 |
| OPERATING CONDITIONS | | | | | | | |
| AVE. REACTOR TEMP., F. | 464 | 451 | 463 | 456 | 450 | 430 | 528 |
| PRESSURE, PSIG | 600 | 600 | 600 | 600 | 600 | 600 | 600 |
| LHSV (TOTAL) | 2.0 | 1.0 | 1.1 | 1.1 | 1.1 | 1.1 | 1.1 |
| LHSV (OLEFIN) | 1.6 | 0.8 | 0.8 | 0.9 | 0.8 | 0.8 | 0.8 |
| WHSV (OLEFIN) | 1.7 | 0.9 | 0.9 | 0.9 | 0.9 | 0.9 | 0.9 |
| OLEFIN CONVERSIONS, WT+ | | | | | | | |
| ETHENE | 100.00 | 100.00 | 100.00 | 100.00 | 100.00 | — | — |
| PROPENE | 100.00 | 100.00 | — | — | — | — | — |
| BUTENE | 72.94 | 31.24 | — | — | 15.76 | — | — |
| PENTENE | 99.01 | 97.36 | 95.92 | 95.70 | 96.61 | 89.69 | 44.66 |
| PRODUCT YIELDS (ON FEED OLEFIN) | | | | | | | |
| TOTAL C4−, WT+ | 0.38 | 0.75 | 1.21 | 0.77 | 1.43 | 6.17 | 2.53 |
| GASOLINE EP, F | 330 | 330 | 330 | 330 | 330 | 330 | 330 |
| LIGHT DISTILLATE EP, F | 650 | 650 | 650 | 650 | 650 | 650 | 650 |
| C5+GASOLINE, WT+ | 9.84 | 10.90 | 12.90 | 12.83 | 15.38 | 40.16 | 73.08 |
| LIGHT DISTILLATE, WT+ | 69.26 | 70.42 | 69.71 | 71.15 | 71.85 | 48.56 | 24.39 |
| HEAVY DISTILLATE, WT+ | 20.52 | 17.93 | 16.18 | 15.25 | 11.35 | 5.11 | 0.00 |
| TOTAL LIQUID PRODUCT, API | 53.4 | 53.9 | 54.4 | 54.8 | 55.7 | 63.8 | 70.0 |
| 5 WT+, F | 137 | 135 | 138 | 137 | 135 | 93 | 93 |
| 10 WT+, F | 154 | 153 | 154 | 156 | 156 | 99 | 99 |
| 30 WT+, F | 329 | 324 | 321 | 320 | 307 | 156 | 136 |
| 50 WT+, F | 451 | 434 | 419 | 404 | 382 | 211 | 162 |
| 70 WT+, F | 551 | 536 | 529 | 519 | 501 | 369 | 210 |
| 90 WT+, F | 696 | 677 | 673 | 661 | 633 | 523 | 383 |
| 95 WT+, F | 755 | 737 | 738 | 730 | 692 | 606 | 423 |

TABLE 13

MATERIAL BALANCE DATA FOR SAMPLE 2

| BALANCE NO. | 1 | 2 | 3 | 4 |
|---|---|---|---|---|
| DAYS ON STREAM | 1 | 2 | 3 | 4 |
| OPERATING CONDITIONS | | | | |
| AVE. REACTOR TEMP., F. | 440 | 426 | 451 | 451 |
| PRESSURE, PSIG | 600 | 600 | 600 | 600 |
| LHSV (TOTAL) | 1.0 | 1.0 | 1.0 | 1.0 |
| LHSV (OLEFIN) | 0.8 | 0.8 | 0.7 | 0.8 |
| WHSV (OLEFIN) | 0.9 | 0.9 | 0.8 | 0.9 |
| OLEFIN CONVERSIONS, WT+ | | | | |
| ETHENE | 100.00 | 100.00 | 100.00 | — |
| PROPENE | 100.00 | — | — | — |
| BUTENE | 61.02 | 28.44 | 46.91 | 34.82 |
| PENTENE | 88.33 | 65.65 | 31.90 | 53.89 |
| PRODUCT YIELDS (ON FEED OLEFIN) | | | | |
| TOTAL C4−, WT+ | 0.50 | 0.55 | 0.23 | 0.43 |
| GASOLINE EP, F | 330 | 330 | 330 | 330 |
| LIGHT DISTILLATE EP, F | 650 | 650 | 650 | 650 |
| C5+ GASOLINE, WT+ | 14.81 | 55.82 | 85.69 | 89.34 |
| LIGHT DISTILLATE, WT+ | 75.70 | 41.06 | 14.07 | 7.67 |
| HEAVY DISTILLATE, WT+ | 8.98 | 2.57 | 0.00 | 2.56 |
| TOTAL LIQUID PRODUCT, API | 57.8 | 66.8 | 73.6 | 75.3 |
| 5 WT+, F | 100 | 97 | 97 | 90 |
| 10 WT+, F | 133 | 102 | 101 | 98 |
| 30 WT+, F | 307 | 152 | 113 | 110 |
| 50 WT+, F | 378 | 169 | 163 | 160 |
| 70 WT+, F | 474 | 347 | 170 | 167 |
| 90 WT+, F | 608 | 433 | 337 | 215 |

TABLE 13-continued

| MATERIAL BALANCE DATA FOR SAMPLE 2 | | | | |
|---|---|---|---|---|
| BALANCE NO. | 1 | 2 | 3 | 4 |
| DAYS ON STREAM | 1 | 2 | 3 | 4 |
| 95 WT+, F | 674 | 526 | 382 | 373 |

TABLE 14

| MATERIAL BALANCE DATA FOR SAMPLE 3 | | |
|---|---|---|
| BALANCE NO. | 1 | 2 |
| DAYS ON STREAM | 1 | 2 |
| OPERATING CONDITIONS | | |
| AVE. REACTOR TEMP., F | 453 | 453 |
| PRESSURE, PSIG | 600 | 600 |
| LHSV (TOTAL) | 1.1 | 1.1 |
| LHSV (OLEFIN) | 0.8 | 0.8 |
| WHSV (OLEFIN) | 1.0 | 0.9 |
| OLEFIN CONVERSIONS, WT+ | | |
| ETHENE | — | 100.00 |
| PROPENE | — | — |
| BUTENE | — | — |
| PENTENE | 38.99 | 43.90 |
| PRODUCT YIELDS (ON FEED OLEFIN) | | |
| TOTAL C4−, WT+ | 0.75 | 0.32 |
| GASOLINE EP, F | 330 | 330 |
| LIGHT DISTILLATE EP, F | 650 | 650 |
| C5+GASOLINE, WT+ | 95.57 | 95.71 |
| LIGHT DISTILLATE, WT+ | 3.68 | 3.97 |
| HEAVY DISTILLATE, WT+ | 0.00 | 0.00 |
| TOTAL LIQUID PRODUCT, API | 73.4 | 74.1 |
| 5 WT+, F | 96 | 96 |
| 10 WT+, F | 101 | 101 |
| 30 WT+, F | 140 | 140 |
| 50 WT+, F | 161 | 161 |
| 70 WT+, F | 166 | 166 |
| 90 WT+, F | 207 | 207 |
| 95 WT+, F | 213 | 213 |

TABLE 15

| MATERIAL BALANCE DATA FOR SAMPLE 4 | | | | | | | | |
|---|---|---|---|---|---|---|---|---|
| Balance No. | 1 | 2 | 3 | 4 | 5 | 6 | 7 | 8 |
| Days on Stream | 1 | 2 | 3 | 4 | 5 | 6 | 8 | 9 |
| Operating Conditions | | | | | | | | |
| Ave. Reactor Temp., F. | 464 | 451 | 463 | 456 | 450 | 430 | 528 | 525 |
| Pressure, PSIG | 600 | 600 | 600 | 600 | 600 | 600 | 600 | 600 |
| LHSV (total) | 2.0 | 1.0 | 1.1 | 1.1 | 1.1 | 1.1 | 1.1 | 1.1 |
| LHSV (olefin) | 1.6 | 0.8 | 0.8 | 0.9 | 0.8 | 0.8 | 0.8 | 0.9 |
| WHSV (olefin) | 1.7 | 0.9 | 0.9 | 0.9 | 0.9 | 0.9 | 0.9 | 1.0 |
| Olefin Conversion, Wt % | | | | | | | | |
| Ethene | 100.00 | 100.00 | 100.00 | 100.00 | 100.00 | — | — | — |
| Propene | 100.00 | 100.00 | — | — | — | — | — | — |
| Butene | 72.94 | 31.24 | — | — | 15.76 | — | — | — |
| Pentene | 99.01 | 97.36 | 95.92 | 95.70 | 96.61 | 89.69 | 44.66 | 35.03 |
| Product Yields (on feed olefin) | | | | | | | | |
| Total C4−, Wt % | 0.38 | 0.75 | 1.21 | 0.77 | 1.43 | 6.17 | 2.53 | 2.03 |
| Gasoline EP, F | 330 | 330 | 330 | 330 | 330 | 330 | 330 | 330 |
| Light Distillate EP, F | 650 | 650 | 650 | 650 | 650 | 650 | 650 | 650 |
| C5+ Gasoline, Wt % | 9.84 | 10.90 | 12.90 | 12.83 | 15.38 | 40.16 | 73.08 | 84.04 |
| Light Distillate, Wt % | 69.26 | 70.42 | 69.71 | 71.15 | 71.85 | 48.56 | 24.39 | 13.93 |
| Heavy Distillate, Wt % | 20.52 | 17.93 | 16.18 | 15.25 | 11.35 | 5.11 | 0.00 | 0.00 |
| Total Liquid Product, API | 53.4 | 53.9 | 54.4 | 54.8 | 55.7 | 63.8 | 70.0 | 72.6 |
| 5 Wt %, F | 137 | 135 | 138 | 137 | 135 | 93 | 93 | 89 |
| 10 Wt %, F | 154 | 153 | 154 | 156 | 156 | 99 | 99 | 95 |
| 30 Wt %, F | 329 | 324 | 321 | 320 | 307 | 156 | 136 | 109 |
| 50 Wt %, F | 451 | 434 | 419 | 404 | 382 | 211 | 162 | 158 |
| 70 Wt %, F | 551 | 536 | 529 | 519 | 501 | 369 | 210 | 166 |
| 90 Wt %, F | 696 | 677 | 673 | 661 | 633 | 523 | 383 | 348 |
| 95 Wt %, F | 755 | 737 | 738 | 730 | 692 | 606 | 423 | 387 |

EXAMPLE 4

The distribution of hexene and pentene isomers in the synthol naphtha feedstock and in selected MOGD products are shown in Tables 16 and 17 in comparison to the calculated equilibrium distribution of isomers.

The MOGD products include those from processing the extracted synthol naphtha over active and deactivwted catalysts, and from processing a model compound blend of $C_5/C_6$ α-olefins without oxygenates. These data reveal that even though oligomerization activity may be quite low due to catalyst deactivation, isomerization activity remains quite high. In all cases, α-olefins ($C_5$, $C_6$) were the major (70+%) isomer form in the feedstock. Isomerization to a distribution that is close to equilibrium occurs even if conversion of the $C_5$ or $C_6$ olefin to higher oligomers is only a few percent due to the low activity of the catalyst.

TABLE 16

HEXENE ISOMER DISTRIBUTION FOR SYNTHOL NAPHTHA SELECTED MOGD PRODUCTS, AND CALCULATED EQUILIBRIUM AT 450° F.

| ISOMER | Synthol Naphtha | 1 | 2 | 3 | Calculated Equilibrium Distribution |
|---|---|---|---|---|---|
| 33DM1B | 0 | 0 | 0 | 0 | 0.13 |
| 4M1P | 10.85 | 1.10 | 0.98 | 0.64 | 0.20 |
| 3M1P | 10.01 | 1.23 | 0.87 | 0.75 | 0.50 |
| 23DM1B | 0.91 | 2.65 | 0.36 | 3.89 | 7.21 |
| C4M2P | 0.11 | 1.28 | 1.41 | 0.91 | 1.90 |
| T4M2P | 0.16 | 4.68 | 5.00 | 3.93 | 3.00 |
| 2M1P | 0 | 7.86 | 7.90 | 6.67 | 9.00 |
| 1H | 71.61 | 2.47 | 1.80 | 6.43 | 0.18 |
| 2E1B | 0.73 | 0 | 1.56 | 0 | 2.03 |
| T3H | 0.34 | 3.38 | 7.61 | 2.30 | 1.11 |
| C3H | 0.17 | 0 | 1.49 | 0 | 0.35 |
| T2H/C | 1.88 | 6.24 | 16.24 | 4.97 | 1.92 |
| 2M2P/C | 0.94 | 22.38 | 22.03 | 20.94 | 30.52 |
| C3M2P | 0.15 | 12.57 | 8.90 | 11.28 | 9.95 |
| C2H | 1.75 | 2.86 | 7.27 | 2.30 | 2.48 |
| T3M2P | 0.31 | 22.30 | 15.52 | 20.30 | 18.66 |
| 23DM2B | 0.07 | 9.00 | 1.05 | 14.66 | 10.87 |

TABLE 16-continued
HEXENE ISOMER DISTRIBUTION FOR SYNTHOL NAPHTHA SELECTED MOGD PRODUCTS, AND CALCULATED EQUILIBRIUM AT 450° F.

| ISOMER | Synthol Naphtha | 1 | 2 | 3 | Calculated Equilibrium Distribution |
|---|---|---|---|---|---|
| Hexene wt % in MOGD Product | | 7.82 | 42.95 | 2.52 | |
| Hexene Converted % | | 82.34 | 3.03 | 93.89 | |

TABLE 17
PENTENE ISOMER DISTRIBUTION

| ISOMER | Synthol Naphtha | 1 | 2 | 3 | Calculated Equilibrium Distribution |
|---|---|---|---|---|---|
| 3M1B | 7.49 | 1.14 | 0.80 | 0.85 | 3.5 |
| 1P | 74.99 | 3.88 | 4.80 | 6.17 | 1.0 |
| 2M1B | 8.60 | 13.44 | 9.11 | 13.72 | 18.3 |
| T2P | 3.77 | 15.73 | 33.37 | 8.33 | 6.7 |
| C2P | 3.77 | 6.73 | 14.14 | 3.47 | 4.5 |
| 2M2B | 1.42 | 59.08 | 37.77 | 67.46 | 66.0 |
| Pentene wt % in MOGD Product | 29.89 | 4.03 | 28.88 | 1.30 | |
| Pentene Converted % | | 86.5 | 3.39 | 97.23 | |

What is claimed is:

1. A process for removing oxygenated impurities including alcohol, aldehyde, ketone or acid from an olefinic hydrocarbon stream comprising a $C_4$–$C_9$ naphtha fraction obtained by Fischer-Tropsch conversion of synthesis gas, said process comprising contacting said hydrocarbon stream under conditions of liquid-liquid extraction with polar organic solvent which comprises approximately equal parts by weight of propylene carbonate and 2-aminoethanol.

2. The process of claim 1 wherein the extracted naphtha, substantially free of oxygenated impurities, is washed with water to remove any of said solvent dissolved therein.

3. The process of claim 2 wherein solvent-containing water is mixed with oxygenate-containing solvent prior to distillation, and the water-solvent mixture is distilled to separate said solvent from said oxygenate impurities.

4. The process of claim 1 wherein 0.5 to 1 volume of solvent is used per volume of hydrocarbon liquid during liquid-liquid extraction.

5. The process of claim 2 wherein extracted naphtha is oligomerized in the presence of a crystalline aluminosilicate zeolite catalyst under conditions to form gasoline and distillate boiling range liquid hydrocarbons.

6. In the process for extracting oxygenated hydrocarbons from olefinic hydrocarbon liquid by contact under liquid extraction conditions with polar organic extraction solvent, the improvement which comprises the use of hydrocarbon-immiscible polar extraction solvent mixture boiling at least 300° C. higher than extracted oxygenates, and having a dipole moment of at least about 0.6 Debye units; said polar extraction solvent comprising 2-aminoalkanol and propylene carbonate having an average dielectric constant of about 30 to 50, boiling above about 172° C.; and dissolving not more than 1% by volume of the olefinic hydrocarbon liquid in an equal volume of said solvent under extraction conditions.

* * * * *